(12) United States Patent
Bauer

(10) Patent No.: US 9,663,441 B2
(45) Date of Patent: May 30, 2017

(54) PROCESS FOR CLEANING CARBON DIOXIDE-CONTAINING PROCESS GASES FROM THE PREPARATION OF VINYL ACETATE

(71) Applicant: Wacker Chemie AG, Munich (DE)

(72) Inventor: Markus Bauer, Burghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 15/301,151

(22) PCT Filed: Mar. 27, 2015

(86) PCT No.: PCT/EP2015/056804
§ 371 (c)(1),
(2) Date: Sep. 30, 2016

(87) PCT Pub. No.: WO2015/150290
PCT Pub. Date: Oct. 8, 2015

(65) Prior Publication Data
US 2017/0022141 A1    Jan. 26, 2017

(30) Foreign Application Priority Data

Apr. 3, 2014  (DE) .................. 10 2014 206 450

(51) Int. Cl.
*C07C 67/48*    (2006.01)
*C07C 67/05*    (2006.01)
(Continued)

(52) U.S. Cl.
CPC .......... *C07C 67/48* (2013.01); *B01D 53/1475* (2013.01); *B01D 53/1493* (2013.01);
(Continued)

(58) Field of Classification Search
CPC ...................................................... C07C 67/48
(Continued)

(56) References Cited

U.S. PATENT DOCUMENTS 4,430,312 A    2/1984  Eickmeyer
8,710,259 B2   4/2014  Dafinger
(Continued)

FOREIGN PATENT DOCUMENTS

DE    102006038689    2/2008
DE    102009002666    10/2010
(Continued)

OTHER PUBLICATIONS

Wunder, R., "CO2-Heiβpottaschewasche—Lehrbuch and Wirklichkeit," "Aqueous potash solutions for the purification of carbon dioxide containing gases," 1988, pp. 410-412, vol. 60, No. 5, Chemie Inaenieur Technik.
(Continued)

*Primary Examiner* — Deborah D Carr
(74) *Attorney, Agent, or Firm* — RatnerPrestia

(57) ABSTRACT

The invention provides processes for cleaning carbon dioxide-containing process gases from the preparation of vinyl acetate after reaction of ethylene with acetic acid and oxygen in heterogeneously catalyzed, continuous gas phase processes, characterized in that carbon dioxide-containing process gases, for removal of carbon dioxide, are contacted with one or more scrubbing solutions, and one or more scrubbing solutions comprise one or more oxides of metals (metal oxides) selected from the group comprising vanadium, niobium, tantalum, chromium, molybdenum, manganese and arsenic.

7 Claims, 1 Drawing Sheet

(51) Int. Cl.
  *B01D 53/62* (2006.01)
  *B01D 53/14* (2006.01)
(52) U.S. Cl.
  CPC .............. *B01D 53/62* (2013.01); *C07C 67/05* (2013.01); *B01D 2251/30* (2013.01); *B01D 2251/40* (2013.01); *B01D 2251/606* (2013.01); *B01D 2252/602* (2013.01); *B01D 2255/1023* (2013.01); *B01D 2255/209* (2013.01); *B01D 2255/2073* (2013.01); *B01D 2255/2092* (2013.01); *B01D 2255/20723* (2013.01); *B01D 2255/20769* (2013.01); *B01D 2255/20784* (2013.01); *B01D 2256/24* (2013.01); *B01D 2258/02* (2013.01)
(58) Field of Classification Search
  USPC ........................................................ 560/248
  See application file for complete search history.

(56) References Cited

U.S. PATENT DOCUMENTS

2007/0032678 A1   2/2007   Stamm
2012/0053361 A1   3/2012   Dafinger

FOREIGN PATENT DOCUMENTS

DE   WO 2010124985 A1 * 11/2010   ........... C07C 67/055
EP   1760065        3/2007
WO   2008019873     2/2008
WO   2010124985     11/2010

OTHER PUBLICATIONS

Ahmadi, M., et al., "Advanced modelling in performance optimization for reactive separation in industrial CO2 removal," Apr. 5, 2008, pp. 107-115, vol. 63, No. 1, Separation and Purification Technology.

Imle, M., et al., "Solubility of carbon dioxide in activated potash solutions in the low and high gas loading regions," Jul. 31, 2013, pp. 13477-13489, vol. 52, No. 37, Industrial & Engineering Chemistry Research.

International Search Report and Written Opinion of the International Searching Authority for International Application No. PCT/EP2015/056804, mailed Jul. 15, 2015, 9 pages.

* cited by examiner

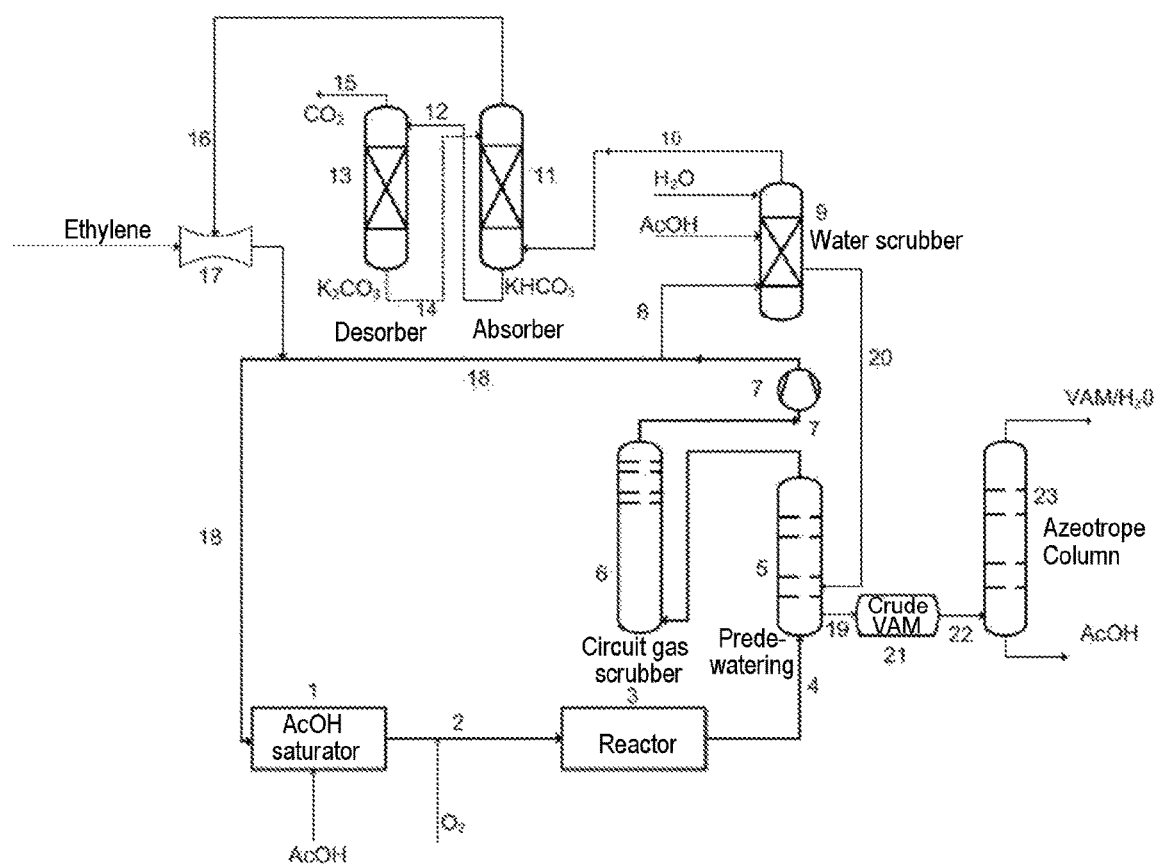

PROCESS FOR CLEANING CARBON DIOXIDE-CONTAINING PROCESS GASES FROM THE PREPARATION OF VINYL ACETATE

CROSS-REFERENCE TO RELATED APPLICATIONS

This application is a U.S. National Phase Application of PCT International Application PCT/EP2015/056804, filed Mar. 27, 2015, which claims priority benefit of German Application DE 10 2014 206 450.3, filed Apr. 3, 2014, the disclosures of which are incorporated herein in their entirety.

BACKGROUND

The invention relates to processes for cleaning carbon dioxide-containing process gases from the preparation of vinyl acetate after reaction of ethylene with acetic acid and oxygen in heterogeneously catalyzed continuous gas-phase processes.

Vinyl acetate is an important monomer building block for the production of polymers such as, for example, vinyl acetate-homopolymers or vinyl acetate-copolymers with ethylene, vinyl chloride, acrylates, maleates, fumarates or vinyl laurate. Vinyl acetate is prepared conventionally in a fixed-bed tubular reactor (or else fluidized-bed reactor) in an exothermic reaction of ethylene with acetic acid and oxygen in heterogeneously catalyzed continuous gas-phase processes. In this case, usually fixed-bed catalysts are used and generally contain palladium salts and alkali metal salts on a support material and in addition can be further doped with gold, rhodium or cadmium. The reaction is usually carried out at a pressure from 1 to 30 bar and a temperature from 130° C. to 200° C.:

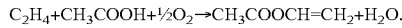

$$C_2H_4 + CH_3COOH + \tfrac{1}{2}O_2 \rightarrow CH_3COOCH=CH_2 + H_2O.$$

In a side reaction, ethylene is oxidized to $CO_2$ (carbon dioxide):

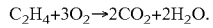

$$C_2H_4 + 3O_2 \rightarrow 2CO_2 + 2H_2O.$$

The greater is the fraction of ethylene which is reacted to form byproducts, the lower necessarily is the selectivity of the reaction of ethylene to form vinyl acetate. Ethylene selectivities that are as high as possible are therefore desirable.

The gas mixture fed to the reactor generally contains a several fold molar excess of ethylene. The reaction of ethylene and the further reagents in the reactor proceeds incompletely. The process gas (product gas stream) taken off from the reactor contains substantially vinyl acetate, ethylene, acetic acid, water, oxygen and also byproducts, predominantly carbon dioxide, and the inerts nitrogen, argon, methane and ethane. From the product gas stream, after it leaves the reactor, the reaction product vinyl acetate, unreacted acetic acid, water and further condensable fractions are condensed out as far as possible and fed to further workup and purification by distillation up to isolation of the pure vinyl acetate. The gas stream remaining after separating off vinyl acetate and condensable fractions from the product gas stream is finally recirculated back to the reactor as circuit gas after further purification steps.

Sufficient ejection of the byproduct carbon dioxide is worthy of particular attention in the purification of the circuit gas. Otherwise, during the continuous operation of the process, an enrichment of carbon dioxide in the circuit gas occurs, as a result of which the vinyl acetate formation in the reactor would be inhibited within a short time. For this reason, in current processes, a part of the circuit gas is branched off before it is recirculated to the reactor and fed to the $CO_2$ scrubber ($CO_2$ absorption/desorption) to separate off $CO_2$ and then combined with the further circuit gas.

The circuit gas is a gas mixture consisting of predominant fractions of ethylene, carbon dioxide, ethane, nitrogen and oxygen. The circuit gas, before recirculation into the fixed-bed tubular reactor, is admixed with the reactants acetic acid, ethylene and oxygen and brought to reaction temperature using heat exchangers operated by heating steam. To compensate for pressure losses, the circuit gas is generally compressed by means of a circuit gas compressor before recirculation to the reactor.

Such processes are known, for example, from DE-A1 102009002666. DE-A 102006038689 describes processes for isolating vinyl acetate from the abovementioned product gas stream, wherein the steam expelled in the $CO_2$ desorber is used energetically. Also EP-A1 1760065 describes processes for isolating vinyl acetate from the product gas stream, wherein the acetic acid produced in the circuit gas scrubber is recycled in a defined manner in the process for vinyl acetate preparation.

Against the background of these developments, also, there continues to be a need to configure the separation of carbon dioxide from the circuit gas to be more efficient, in particular less energy-intensive.

The $CO_2$ scrubber of the circuit gas has been operated for many decades generally using aqueous potash solutions. For improved separation of carbon dioxide from gases, in recent years also in connection with the storage of carbon dioxide, also termed Carbon Capture and Storage (CCS), a number of relatively efficient absorption media or additives have been developed such as, for example, methylamine or ethanolamine. Such new developments from other technologies, however, are not simply transferrable to processes for cleaning circuit gas of vinyl acetate preparation, since in this case interventions are made into a complex gas mixture, whose composition has been further optimized for decades. It would also be fatal, if, by modifying the absorption medium, impurities were to be introduced into the circuit gas and further utilization or reaction of the circuit gas would be impaired.

SUMMARY

Against this background, the object was to configure the separating off of $CO_2$ from the process gases of the vinyl acetate preparation so as to be more efficient, in particular less energy intensive.

The invention relates to processes for cleaning carbon dioxide-containing process gases from the preparation of vinyl acetate after reaction of ethlene with acetic acid and oxygen in heterogeneously catalyzed continuous gas-phase processes, characterized in that carbon dioxide-containing process gases, for removing carbon dioxide, are contacted with one or more scrubbing solutions and one or more scrubbing solutions contain one or more oxides of metals (metal oxides) selected from the group comprising vanadium, niobium, tantalum, chromium, molybdenum, manganese and arsenic.

BRIEF DESCRIPTION OF THE DRAWINGS

FIG. 1 is a schematic diagram of certain aspects of a process for the production of vinyl acetate pertaining to the invention.

DETAILED DESCRIPTION

Process gas can refer to any gas composition of the process according to the invention. The specific composition and the further properties of a process gas at a defined point of the process are established by the process conditions according to which the respective process gas was generated or treated. Corresponding information is described hereinafter with further details.

The metals are preferably present in their highest oxidation state. The oxidation states are therefore preferably five in the case of vanadium, niobium, tantalum or arsenic, six in the case of chromium or molybdenum, or seven in the case of manganese. Examples thereof are $Nb_2O_5$, $Ta_2O_5$, $As_2O_5$, $CrO_3$, $MoO_3$, $Mn_2O_7$ and in particular $V_2O_5$. The preferred metal of the metal oxides is vanadium. Preference is also given to salts of the metal oxides, in particular the alkaline earth metal salts or alkali metal salts thereof, such as, for example, or $KVO_3$, $NaVO_3$, $KV_2O_5$, $Na_4V_2O_7$, $K_4V_2O_7$ or $K_2Cr_2O_7$. The metal oxides or salts thereof can be present in the scrubbing solutions in a manner known per se as monomers, dimers or oligomers, dissociated or undissociated.

A scrubbing solution preferably contains 0.5 to 20% by weight, particularly preferably 2 to 15% by weight, and most preferably 3 to 10% by weight, of metal oxides, based on the total weight of the scrubbing solution. The metal oxides, in particular in the abovementioned amounts, are generally soluble in the scrubbing solutions under standard conditions as specified by DIN50014.

Preference is also given to scrubbing solutions that contain at least two oxides of metals, in particular oxides of vanadium, niobium, tantalum or chromium (group I) and in addition oxides of boron, aluminum or arsenic (group II). Examples of corresponding oxides of boron are $B(OH)_3$, $KBO_2$, $Na_2B_2O_4$, $K_2B_2O_4$. $Na_2B_2O_7$ or $K_2B_2O_7$. Examples of further oxides are already listed further above.

Preferred scrubbing solutions contain 0.5 to 15% by weight, particularly preferably 2 to 10% by weight, and most preferably 3 to 8% by weight of metal oxides of group I and 1 to 10% by weight, particularly preferably 1 to 8% by weight, and most preferably 2 to 6% by weight of metal oxides of group II, in each case based on the total weight of the scrubbing solution. The weight ratio of the metal oxides of group I to the metal oxides of group II is preferably 1:2 to 4:1, and particularly preferably 1:1 to 2:1.

The scrubbing solutions are generally aqueous. The scrubbing solutions preferably do not contain any organic solvents, such as amines, in particular no alkanolamines or alkylamines, such as methylamines, ethanolamines, propanolamines or butanolamines.

The scrubbing solution is generally an alkaline medium, in particular an alkaline solution. The scrubbing solutions preferably also contain (alkaline earth) alkali metal hydroxides or preferably (alkaline earth) alkali metal carbonates, in particular potassium carbonate. The scrubbing solutions preferably contain 15 to 40% by weight, and particularly preferably 20 to 30% by weight, of (alkaline earth) alkali metal hydroxides, based on the total weight of a scrubbing solution.

The scrubbing solution is preferably situated in a $CO_2$ absorber. The $CO_2$ absorber is hereinafter also referred to as $CO_2$ scrubber. $CO_2$ scrubbing represents the cleaning according to the invention of processes gases with $CO_2$ scrubbers, that is to say for the removal or separating off of carbon dioxide from a process gas. As $CO_2$ absorbers, the plants familiar in the technical field can be used. $CO_2$ absorbers customarily have the form of columns, in particular distillation columns.

The process gas from which the carbon dioxide is to be removed is commonly fed to the $CO_2$ absorber in the region of the sump thereof. Carbon dioxide is taken off from the carbon dioxide-containing process gas in the course of passage through the $CO_2$ absorber. Carbon dioxide is taken up by the scrubbing solution, for example chemically or physically bound. In this manner, the process gas can at least be partly freed from carbon dioxide. The process gas thus cleaned is usually withdrawn at the top of the $CO_2$ absorber and finally fed back to the reactor for further reaction to form vinyl acetate. Usually, the circuit gas, before it is introduced into the reactor, is charged with ethylene, acetic acid and/or oxygen, and also if necessary compressed and/or brought to the desired temperature.

The carbon dioxide-containing process gas that is introduced into the $CO_2$ absorber preferably contains 10 to 20% by weight, in particular 13 to 19% by weight, of carbon dioxide, 55 to 70% by weight, in particular 60 to 70% by weight of ethylene, and also other usual amounts of the inerts, such as ethane, methane, nitrogen or argon, and also optionally other components, wherein the figures in % by weight relate to the total weight of this process gas. The cleaned process gas that leaves the $CO_2$ absorber preferably contains less $\leq 2.5\%$ by weight, particularly preferably $\leq 2\%$ by weight, and most preferably $\leq 1.6\%$ by weight, but generally $\geq 0.5\%$ by weight, of carbon dioxide and also preferably 70 to 95% by weight, and particularly preferably 75 to 85% by weight, of ethylene and other usual amounts of the inerts, such as ethane, methane, nitrogen or argon, and optionally also other usual components, wherein the figures in % by weight relate to the total weight of the cleaned process gas leaving the $CO_2$ absorber. In the cleaning according to the invention, therefore, in particular carbon dioxide is removed from the process gas.

The pressure of the process gas when it enters into the $CO_2$ absorber is customarily 9 to 10 bar. In the $CO_2$ absorber, generally temperatures from 95 to 100° C. prevail.

The sump of the $CO_2$ absorber, that is to say the part of the scrubbing solution that is produced at the sump of the $CO_2$ absorber and is loaded with carbon dioxide, is usually fed to a $CO_2$ desorber. The scrubbing solution introduced into the $CO_2$ desorber is heated in the $CO_2$ desorber customarily to 100 to 120° C. and freed from carbon dioxide. Carbon dioxide that is liberated is ejected from the process. In the sump of the $CO_2$ absorber, as is usual, a scrubbing solution that is at least partly freed from carbon dioxide is produced. The scrubbing solution produced at the sump of the $CO_2$ desorber is generally at least in part withdrawn and recirculated to the $CO_2$ absorber in the region of the top.

In a preferred embodiment, the $CO_2$ absorber of the $CO_2$ desorber contains packings, such as Pall rings, Berl saddles, Hiflow rings, Intalox saddles, hedgehogs or in particular Raschig rings. Alternatively, the $CO_2$ absorber or the $CO_2$ desorber can also be equipped with mass-transfer trays, preferably sieve trays.

Otherwise, the $CO_2$ absorber and the $CO_2$ desorber can be constructed and operated according to the prior art.

The water scrubber is generally integrated upstream of the $CO_2$ absorber into the circuit process, that is to say the process gas is usually conducted first through a water scrubber and then introduced into a $CO_2$ absorber; or in other words, the water scrubber is generally situated between the point at which the process gas is withdrawn from a circuit gas substream or is branched off, and the entry of this circuit gas substream into the $CO_2$ absorber. The process gas is usually introduced into the water scrubber in the region of the sump. The water scrubber is generally charged with acetic acid and water. Vinyl acetate, for example, is thereby scrubbed from the process gas. The process gas thus purified can be withdrawn at the top of the water scrubber and introduced into the $CO_2$ absorber.

Hereinafter, the process for producing vinyl acetate and the separation according to the invention of carbon dioxide from a process gas or from the circuit gas is described with further details.

In the continuous preparation of vinyl acetate, preferably operations proceed in tubular reactors that are charged with a fixed-bed catalyst. These catalysts are generally supported catalysts doped with noble metals or noble metal salts, and promoters, for example bentonite spheres doped with palladium and with gold and potassium salts. The reactor is charged with ethylene, oxygen and acetic acid, and the reaction is carried out at a pressure from preferably 8 to 12 bar abs., and at a temperature from preferably 130° C. to 200° C.

The reaction temperature in the fixed-bed tubular reactor from preferably 130° C. to 200° C. is preferably established by means of boiling water cooling at a pressure from 1 to 30 bar abs. In this case, steam, what is termed inherent steam, is formed at a temperature of from for example 120° C. to 185° C. at a pressure from 1 to 10 bar abs., preferably 2.5 to 5 bar abs. The product gas exiting from the reactor contains substantially vinyl acetate, ethylene, acetic acid, water, oxygen, $CO_2$ and also the inerts nitrogen, argon, methane and ethane.

Generally, the gas mixture leaving the fixed-bed tubular reactor is passed into a predewatering column and the liquid phase arising at the sump of the column, principally vinyl acetate, acetic acid, ethyl acetate and water, is fed to the crude vinyl acetate collecting vessel. Usually, in a downstream azeotropic column the mixture is separated into vinyl acetate monomer (VAM) and water as overhead product, and acetic acid as sump product. The acetic acid can be passed into the acetic acid saturator and thus recirculated to the process. The VAM withdrawn as overhead product can be passed via the dewatering column to the pure vinyl acetate column and there separated into VAM and acetic acid.

The gaseous mixture that is withdrawn overhead from the predewatering column and substantially consists of ethylene and $CO_2$ is usually freed in the circuit gas scrubber from further, possibly from all, condensable fractions. The circuit gas withdrawn overhead from the circuit gas scrubber is usually compressed in the circuit gas compressor, to compensate for the pressure drops occurring in the reaction circuit, and recirculated back as circuit gas to the reactor. The pressure level of the circuit gas is preferably 8 to 12 bar abs.

A substream of the circuit gas (circuit gas substream) is preferably branched off on the suction side or pressure side, in particular the pressure side, of the circuit gas compressor and fed to the $CO_2$ removal that is essential to the invention of the $CO_2$ scrubbing and, after the $CO_2$ removal, passes back to the compressor as usual on the pressure side. The substream withdrawn at the circuit gas compressor makes up, for example, 8 to 20% by volume of the total circuit gas. In alternative embodiments of the process, 8 to 12% by volume or more than 12 to 18% by volume of the total circuit gas can be withdrawn at the circuit gas compressor. Customarily, after the branching off, and before the $CO_2$ scrubbing, the substream that is withdrawn is scrubbed in a column (water scrubber) with feed of water and acetic acid.

The liquid sump product can be collected in the crude vinyl acetate container and separated in the downstream azeotropic column. The gaseous overhead product of the water scrubber, substantially ethylene and $CO_2$, is fed to the $CO_2$ scrubber.

The circuit gas substream (overhead product of the water scrubber) is then preferably conducted into a $CO_2$ absorber, also termed $CO_2$ scrubber.

The circuit gas substream is generally combined with the further circuit gas downstream of the $CO_2$ scrubber, on the pressure side of the circuit gas compressor and downstream of the withdrawal point of the substream for the $CO_2$ scrubber. Generally, to compensate for the pressure drop, the circuit gas substream is brought to a pressure level of preferably 0.5 to 2 bar above the pressure of the circuit gas, by means of ethylene, which is available, for example, at a pressure of 15 to 25 bar abs. and fed to the circuit gas. Preferably, the circuit gas substream is fed with the required amount of ethylene via a jet compressor (ejectors, injectors), preferably a suction nozzle. In a preferred embodiment a procedure can also be followed such that the entire ethylene feed which is fed upstream of the reactor to the circuit gas is fed via the jet compressor.

The use according to the invention of metal oxides achieves a considerable production increase and energy saving in the production and purification of vinyl acetate. For instance, in the procedure according to the invention, in comparison with conventional processes, the fraction of the circuit gas that is to be purified in the $CO_2$ scrubber can be reduced, without having to accept adverse effects on degree of purity or the composition of the circuit gas. Since, in this manner, lower amounts of liquid need to be circulated, considerable savings in equipment and energy are associated herewith. Thus, for example the energy expenditure for pumping the liquid in circulation and the need for heating steam are reduced.

If, in the process according to the invention, as an alternative, the same fractions of the circuit gas are cleaned in a $CO_2$ scrubber as in the prior art, that is to say if the same effort is made as in the prior art, then in the procedure according to the invention, in comparison with the conventional procedure, a greater cleaning effect is achieved. As a result, circuit gas can be obtained at a higher ethylene content and vinyl acetate can be prepared more efficiently. These advantages also come into effect when the capacity of a plant for vinyl acetate preparation is to be increased and thereby larger amounts of the byproduct carbon dioxide are produced and are to be ejected from the circuit process.

Advantageously, in the course of the use according to the invention of metal oxides, no substances or at least no significant amounts of substances, such as catalyst poisons, are introduced into the circuit gas that are harmful for further reaction thereof in the reactor to form vinyl acetate.

The examples hereinafter serve to further illustrate the invention, without restricting the invention in any way:

General Process Description:

In a plant according to FIG. 1, ethylene-containing circuit gas is charged with acetic acid (AcOH) in the acetic acid saturator 1 (AcOH saturator), thereafter oxygen ($O_2$) is added and fed to the tubular reactor 3 via a steam heated line 2. The circuit gas mixture leaving the reactor, which mixture substantially contained ethylene, vinyl acetate, acetic acid, carbon dioxide, oxygen and also inerts, was fed via line 4 to the predewatering column 5. In the predewatering column 5, the mixture was separated, wherein the sump product substantially containing VAM, acetic acid and water ($H_2O$) was fed to the crude vinyl acetate container 21 via line 19, and, after transfer via line 22 to the azeotrope column 23 was separated into a VAM fraction and an acetic acid fraction each of which were further worked up in process steps that are not shown here.

The overhead product of the predewatering column 5 was withdrawn and freed from gaseous VAM in the downstream circuit gas scrubber 6 by means of scrubbing with acetic acid. The gas mixture (circuit gas) was compressed with the circuit gas compressor 7 to a pressure about 3 bar higher. The majority of the circuit gas was recirculated via 18 to the acetic acid saturator 1.

A fraction of 12 or 18% by volume of the circuit gas, as stated in the table for the respective (comparative) example, was branched off on the pressure side from the circuit gas compressor 7 and transferred via line 8 to the water scrubber 9 and there, to remove further vinyl acetate, was treated with acetic acid and then water. The bottoms product comprising acetic acid, water and vinyl acetate was introduced via line 20 directly into the predewatering column 5.

The overhead product of the water scrubber 9 was passed via line 10 in the region of the sump at a rate of 10 tonnes per hour into the $CO_2$ absorption column 11. The $CO_2$ absorption column 11 was operated at a circulation rate of 90 tonnes per hour or 45 tonnes per hour of a 25% strength by weight aqueous potassium carbonate scrubbing solution that optionally contained 6% by weight of potassium vanadate and 4% by weight of potassium borate as additives, as specified in more detail in the table. Otherwise, the $CO_2$ absorption column 11 and the $CO_2$ desorption column 13 were operated in a conventional manner.

The sump of the $CO_2$ absorption column 11 contained, as usual, potassium hydrogen carbonate and was passed via line 12 to the top of the $CO_2$ desorption column 13. The sump of the $CO_2$ desorption column 13 contained potassium carbonate and was introduced via line 14 in the region of the top into the $CO_2$ absorption column 11. The mass flow rate transferred from the $CO_2$ absorption column 11 into the desorption column 13 corresponded to the mass flow rates transferred from the desorption column 13 to the $CO_2$-absorption column 11. The scrubbing solution introduced into the $CO_2$-desorption column 13 was heated by means of heating steam and thereby freed from carbon dioxide. The heating steam rates used in the respective (comparative) example are stated in the table. Via line 15, $CO_2$ was removed from the desorption column 13.

The overhead product of the $CO_2$-absorption column 11 was passed via the line 16 into the ejector 17, there admixed with ethylene feed and finally introduced via the acetic acid saturator 1 into the reactor 3.

Comparative example 1 (CEx.1) and example 2 (Ex.2) make it clear that the addition according to the invention of potassium vanadate and potassium borate considerably increases the efficiency of the circuit gas scrubbing in the $CO_2$-absorption column 11. As a result, the circulation rates of the potassium carbonate solution scrubbing solution in the $CO_2$-absorption column 11 and the required heating steam rate in the $CO_2$-desorption column 13 were able to be halved, and moreover with separation of carbon dioxide retained, as the $CO_2$ concentration in the circuit gas before entry into the acetic acid saturator 1 indicates in the table. As a result, the energy requirement in the process according to the invention can be reduced in comparison with the conventional process.

TABLE

|  | CEx. 1 | Ex. 2 | Ex. 3 |
|---|---|---|---|
| Fraction of the circuit gas transferred into the water scrubber 9 [% by volume] | 12 | 12 | 18 |
| Circulation rate of the potassium carbonate scrubbing solution in the $CO_2$-absorption column 11 [t/h] | 90 | 45 | 90 |
| Additions to the scrubbing solution: |  |  |  |
| Potassium vanadate $KVO_3$ | – | + | + |
| Potassium borate $KBO_2$ | – | + | + |
| Heating steam rate introduced into the $CO_2$-desorption column 13 [t/h] | 4.5 | 2.3 | 4.5 |
| $CO_2$ concentration of the process gas that was fed to the water scrubber 9 via line 8 [% by volume] | 20 | 20 | 20 |
| $CO_2$ concentration in the circuit gas before entry into the acetic acid saturator 1 [% by volume] | 18.3 | 18.3 | 17.5 |

Comparison of example 3 (Ex.3) and comparative example 1 shows that the capacity of the scrubbing solution according to the invention, in comparison with a conventional scrubbing solution, is considerably increased, in such a manner that with otherwise identical mode of operation to that in the prior art, 50% more circuit gas can be introduced via the water scrubber 9 into the $CO_2$-absorption column 11 and freed from carbon dioxide, without additional expenditure in terms of apparatus and energy being incurred thereby. As a result, finally, the ethylene content of the circuit gas can be increased, for example, before entry into the acetic acid saturator 1, and thereby also on entry into the reactor.

This specifically means that, in example 3, by introducing a larger fraction of the circuit gas into the water scrubber 9 and thereby also into the $CO_2$-absorption column 11, in the cleaning that is performed there, the carbon dioxide fraction was decreased from 19% by weight to below 3% by weight of carbon dioxide and in total 50% more carbon dioxide were removed than in the comparative example 1. Finally, the consequence was that the carbon dioxide content in the circuit gas was decreased by cleaning from 18.3% by weight in the comparative example 1 to 17.5% by weight in example 3. The circuit gas volume no longer demanded by carbon dioxide was made up by ethylene on the ejector 17 in such a manner that the ethylene content before entry into the acetic acid saturator 1 was increased by 0.8% by weight.

The invention claimed is:

1. A process for cleaning carbon dioxide-containing process gases from the preparation of vinyl acetate, comprising the steps of: reacting ethylene with acetic acid and oxygen in a heterogeneously catalyzed continuous gas-phase process to form a
    carbon dioxide-containing process gas; and contacting the carbon dioxide-containing process gas with one or more alkaline scrubbing solutions
    comprising:
    I) one or more oxides of metals form the group comprising $KVO_3$, $NaVO_3$, $KV_2O_5$, $Na_4V_2O_7$ and $K_4V_2O_7$ and also
    II) one or more oxides of metals of the group comprising $KBO_2$, $Na_2B_2O_4$, $K_2B_2O_4$, $Na_2B_2O_7$ and $K_2B_2O_7$.

2. The process of claim 1, wherein the one or more scrubbing solutions are situated in a $CO_2$ absorber having a sump, said process further comprising the steps of: feeding the carbon dioxide-containing process gas to the $CO_2$ absorber in the region of the sump thereof; passing the carbon dioxide-containing process gas through the $CO_2$ absorber whereby carbon dioxide is removed from the process gas and is taken up by the scrubbing solution; and withdrawing the cleaned process gas from the $CO_2$ absorber and feeding it back to the reaction forming vinyl acetate.

3. The process of claim 1, wherein the one or more scrubbing solutions contain 0.5 to 20% by weight of oxides of metals, based on the total weight of the scrubbing solution.

4. The process of claim 1, wherein the one or more scrubbing solutions contain 0.5 to 15% by weight of oxides of metals of group I and 1 to 10% by weight of oxides of metals of group II, in each case based on the total weight of the scrubbing solution.

5. The process of claim 1, wherein the scrubbing solutions have a weight ratio of the oxides of metals of group I to the oxides of metals of group II of 1:2 to 4:1.

6. The process of claim 1, wherein the one or more scrubbing solutions contain alkaline earth metal hydroxides, alkali metal hydroxides, alkaline earth metal carbonates or alkali metal carbonates.

7. The process of claim 2, wherein the cleaned process gas withdrawn from the $CO_2$ absorber contains ≤1.6% by weight of carbon dioxide, 70 to 95% by weight of ethylene, and further amounts of inerts selected from the group consisting of ethane, methane, nitrogen, and argon, wherein % by weight is based on the total weight of the cleaned process gas withdrawn from the $CO_2$ absorber.

* * * * *